US008871200B2

(12) United States Patent
Genkin et al.

(10) Patent No.: US 8,871,200 B2
(45) Date of Patent: Oct. 28, 2014

(54) METHOD FOR TREATING HUMAN DISEASES ASSOCIATED WITH AN INCREASED DEOXYRIBONUCLEIC ACID CONTENT IN EXTRACELLULAR SPACES OF TISSUES AND A MEDICINAL PREPARATION FOR CARRYING OUT SAID METHOD

(75) Inventors: Dmitry Dmitrievich Genkin, Saint-Petersburg (RU); Viktor Veniaminovich Tets, Saint-Petersburg (RU); Georgy Viktorovich Tets, Saint-Petersburg (RU)

(73) Assignee: CLS Therapeutics Limited, Guernsey, Channel Islands (GB)

( * ) Notice: Subject to any disclaimer, the term of this patent is extended or adjusted under 35 U.S.C. 154(b) by 823 days.

(21) Appl. No.: 12/516,440

(22) PCT Filed: Nov. 28, 2006

(86) PCT No.: PCT/RU2006/000642
§ 371 (c)(1), (2), (4) Date: May 27, 2009

(87) PCT Pub. No.: WO2008/066403
PCT Pub. Date: Jun. 5, 2008

(65) Prior Publication Data
US 2010/0061971 A1 Mar. 11, 2010

(51) Int. Cl.
A61K 38/43 (2006.01)
A61K 38/46 (2006.01)
A61K 38/47 (2006.01)
A61K 9/00 (2006.01)
A61K 9/68 (2006.01)
A61K 9/20 (2006.01)

(52) U.S. Cl.
CPC ............. *A61K 38/465* (2013.01); *A61K 38/47* (2013.01); *A61K 38/46* (2013.01); *A61K 38/43* (2013.01); *A61K 9/0031* (2013.01); *A61K 9/0058* (2013.01); *A61K 9/2018* (2013.01); *A61K 9/2054* (2013.01); *C12Y 301/21001* (2013.01)
USPC ...................... 424/94.61; 424/94.1; 424/94.6

(58) Field of Classification Search
USPC ..................................... 424/94.1, 94.6, 94.61
See application file for complete search history.

(56) References Cited

U.S. PATENT DOCUMENTS

| 4,485,095 | A | 11/1984 | Fujisaki et al. |
| 5,484,589 | A | 1/1996 | Salganik |
| 5,656,589 | A | 8/1997 | Stossel et al. |
| 5,889,153 | A | 3/1999 | Suzuki et al. |
| 5,952,170 | A | 9/1999 | Stroun et al. |
| 6,033,846 | A | 3/2000 | Fournie |
| 6,156,504 | A | 12/2000 | Gocke et al. |
| 6,391,607 | B1 | 5/2002 | Lazarus et al. |
| 6,428,785 | B1 | 8/2002 | Gokcen |
| 6,455,250 | B1 | 9/2002 | Aguilera et al. |
| 6,465,177 | B1 | 10/2002 | Hoon |
| 6,521,409 | B1 | 2/2003 | Gocke et al. |
| 7,612,032 | B2 | 11/2009 | Genkin et al. |
| 2003/0044403 | A1 | 3/2003 | Shak |
| 2004/0001817 | A1 | 1/2004 | Giampapa |
| 2004/0157239 | A1* | 8/2004 | Tanuma et al. ................ 435/6 |
| 2006/0228347 | A1 | 10/2006 | Sunaga et al. |
| 2006/0233780 | A1 | 10/2006 | Genkin et al. |
| 2007/0104702 | A1 | 5/2007 | Genkin et al. |
| 2008/0004561 | A1 | 1/2008 | Genkin et al. |
| 2009/0047272 | A1* | 2/2009 | Appelbaum et al. ....... 424/94.61 |
| 2009/0053200 | A1 | 2/2009 | Genkin et al. |
| 2010/0150903 | A1 | 6/2010 | Genkin et al. |
| 2010/0303796 | A1 | 12/2010 | Genkin et al. |
| 2011/0033438 | A1 | 2/2011 | Bartoov et al. |
| 2011/0070201 | A1* | 3/2011 | Shaaltiel et al. ............ 424/93.7 |
| 2011/0189156 | A1 | 8/2011 | Genkin et al. |

FOREIGN PATENT DOCUMENTS

| CA | 2394856 | 6/2001 |
| CA | 2184582 | 12/2001 |
| DE | 4024530 | 2/1992 |
| DE | 10221194 | 12/2003 |
| EP | 0325191 | 7/1989 |
| EP | 1655036 | 5/2006 |
| EP | 1661579 | 5/2006 |
| EP | 1880733 | 1/2008 |
| GB | 984464 | 2/1965 |

(Continued)

OTHER PUBLICATIONS

SIGMA Product Information sheet for Deoxyribonuclease I from Bovine Pancreas, 2006.*
Sherry et al., Presence and Significance of Desoxyribose Nucleoprotein in the Purulent Pleural Exudates of Patients, Proc. Soc. Exp. Biol. Med., 1948, 68:179-84.
Lee, David, Continued Marketing of a Useless Drug ('Varidase') in Panama, Lancet, Mar. 1990, vol. 335, p. 667.

(Continued)

*Primary Examiner* — Anne-Marie Falk
(74) *Attorney, Agent, or Firm* — Troutman Sanders LLP

(57) ABSTRACT

The invention relates to medicine. The invention provides inventive method for treating human diseases associated with an increased deoxyribonucleic acid content in extracellular spaces of tissues and organs, which method comprises enterally administering DNAse enzyme in a quantity of 20 000-500 000 Kunz units in a day per 1 kg of the body mass. The single dose of the inventive medicinal preparation for treating human diseases associated with an increased deoxyribonucleic acid content in extracellular spaces of tissues and organs comprises 20 000-500 000 Kunz units of the DNAse enzyme. The oral administration of the above-mentioned important doses of the preparation allows the catalytically significant amount of DNAse to be absorbed into the systemic circulation in such a way that the dose-dependent treating effect thereof is exhibited.

8 Claims, No Drawings

(56) References Cited

FOREIGN PATENT DOCUMENTS

| | | |
|---|---|---|
| GB | 1005985 | 9/1965 |
| JP | 61293927 | 12/1986 |
| JP | 2006-290769 | 10/2006 |
| NZ | 299257 | 8/2000 |
| RU | 2099080 | 12/1997 |
| RU | 2001104426 | 1/2003 |
| RU | 2202109 | 4/2003 |
| RU | 2207676 | 7/2003 |
| RU | 2207876 | 7/2003 |
| RU | 2239404 | 11/2004 |
| RU | 2239442 | 11/2004 |
| RU | WO2005007187 | 1/2005 |
| RU | 2267329 | 1/2006 |
| RU | 2269356 | 2/2006 |
| RU | 2269357 | 2/2006 |
| RU | 2269358 | 2/2006 |
| RU | 2269359 | 2/2006 |
| RU | 2308968 | 10/2007 |
| WO | WO93/03709 | 3/1993 |
| WO | WO95/00170 | 1/1995 |
| WO | WO97/28266 | 8/1997 |
| WO | WO97/47751 | 12/1997 |
| WO | WO00/03709 | 1/2000 |
| WO | WO00/31238 | 6/2000 |
| WO | WO01/74905 | 10/2001 |
| WO | WO 03/068254 * | 8/2003 |
| WO | WO 2005/004903 * | 1/2005 |
| WO | WO2005004789 | 1/2005 |
| WO | WO2005004903 | 1/2005 |
| WO | WO2005004904 | 1/2005 |
| WO | 1666055 | 2/2005 |
| WO | WO2005/115444 | 12/2005 |
| WO | WO2006/130034 | 12/2006 |
| WO | WO2008/047364 A2 | 4/2008 |
| WO | WO2008/066403 | 6/2008 |
| WO | WO2011/073665 | 6/2011 |
| WO | WO2012/075506 | 6/2012 |

OTHER PUBLICATIONS

Oliven et al., Orally and Rectally Administered Streptokinase, Pharmacology, 1981, vol. 22, pp. 135-138.

Department of Health and Human Services Food and Drug Administration, Federal Register, Dec. 13, 1985, vol. 50, No. 240.

Anker, P. et al., Tumor-related alterations in circulating DNA, potential for diagnosis, prognosis and detection of minimal residual disease, Leukemia, 15, 289-91, 2001.

Ashton, G., Growing pains for biopharmaceuticals, Nature Biotech, vol. 19, pp. 307-311, 2001.

Aung et al., Current status and future potential of somatic mutation testing from circulating free DNA in patients with solid tumours, HUGO J, vol. 4, pp. 11-21, 2010.

Boyko et al., Cell-free DNA—a marker to predict ischemic brain damage in a rat stroke experimental model, Journal of Neurosurgical Anesthesiology, vol. 23, pp. 222-228, 2011.

Burt et al., Detection of circulating donor deoxyribonucleic acid by microsatellite analysis in a liver transplant recipient, Liver Transpl Surg, vol. 2, pp. 391-394, 1996.

Davis JC et al., Recombinant human Dnase I (rhDNase) in patients with lupus nephritis, Lupus, vol. 8, pp. 68-76, 1999.

Deocharan B., et al., Alpha-actinin is a cross-reactive renal target for pathogenic anti-DNA antibodies, J. Immunol, vol. 168, pp. 3072-3078, 2002.

Dittmar, Manuela et al., A novel mutation in the *DNASE1* gene is related with protein instability and decreased enzyme activity in thyroid autoimmunity, Journal of Autoimmunity, vol. 32, pp. 7-13, 2009.

El Hassan No, et al. Rescue use of Dnase in critical lung atelectasis mucus retention in premature neonates, Pediatrics., vol. 108, pp. 468-470, 2001.

Freshney, R. I., Culture of Animal Cells, A Manual of Basic Technique, Alan R. Liss, Inc., New York, pp. 3-4, 1983.

Gannushkina, LV., et al., Plasma DNA Levels in Patients with Atherosclerotic Involvement of the Major Arteries of the Head and lateral Amyotrophic Sclerosis, Bulletin of Experimental Biology and Medicine, vol. 124, pp. 1164-1166, 1997 (Translated from: Gannushkina LV. et al., Uroven DNK v plazme krovi bolnykh s arteroskleroticheskim porazheniem magistralnykh artery golovy I bokovym amiotroficheskim sklerozom, Byulleten' Experimental'noi Biologii i Meditsiny, Moscow, Meditsina, No. 12, pp. 610-612, 1997).

Gibbs et al., Mechanism-Based Target Identification and Drug Discovery in Cancer Research Science, vol. 287, pp. 1969-1973, 2000.

Gormally et al., Circulating free DNA in plasma or serum as biomarker of carcinogenesis: Practical aspects and biological significance, Mutation Research, vol. 635, pp. 105-117, 2007.

Gorrini, C., et al., Effect of apoptogenic stimuli on colon carcinoma cell lines with a different c-myc expression level, Int J Mol Med, vol. 11, pp. 737-742, 2003.

Gura, T., Systems for identifying New Drugs Are Often Faulty, Science, vol. 278, pp. 1041-1042, 1997.

Hann, et al. Building 'validated' mouse models of human cancer. Curr Opin Cell Biol, vol. 13, pp. 778-784, 2001.

Horlitz, M., et al., Optimized Quantification of Fragmented, Free Circulating DNA in Human Blood Plasma Using a Calibrated Duplex Real-Time PCR, PLoS ONE, vol. 4, Issue 9, e7207, 2009.

Huttunen, R., et al., Fatal Outcome in Bacteremia is Characterized by High Plasma Cell Free DNA Concentration and Apoptotoc DNA Fragmentation: A Prospective Cohort Study, PLoS ONE, vol. 6, e21700, 2011.

International Search Report for PCT/RU2003/000304, mailed on Mar. 25, 2004.

International Search Report for PCT/RU2004/000260, mailed on Dec. 9, 2004.

International Search Report for PCT/RU2004/000261, mailed on Oct. 21, 2004.

International Search Report for PCT/RU2004/000262, mailed on Oct. 21, 2004.

International Search Report for PCT/RU2005/000236, mailed on Nov. 24, 2005.

Juncosa, B., DNA on the Loose: Next-Gen Blood Tests Tap Free-Floating Genetic Material, Scientific American, Mar. 18, 2009.

Jylhava et al., Aging is associated with quantitative and qualitative changes in circulating cell-free DNA: the Vitality 90+ study, Mechanisms of Ageing and Development, vol. 132, pp. 20-26, 2011.

Kawane, K, et at, DNAse II deficiency causes chronic polyarthritis in mice, Nature Clinical Practice Rheumatology, vol. 3, p. 192, 2007.

Krapf F. et al., The estimation of circulating immune complexes, C3d, and anti-ds-DNA-antibody serum levels in the monitoring of therapeutic plasmapheresis in a patient with systemic lupus erythematosus. A case report, Clin Exp Rheumatol., vol. 3, pp. 159-162, 1985.

Lachmann PJ, Lupus and Desoxyribonuclease, Lupus, vol. 12, pp. 202-206, 2003.

Leland et al., Cancer chemotherapy—ribonucleases to the rescue, Chem. & Bio., vol. 8, pp. 405-413, 2001.

Leon et al., Free DNA in the Serum of Cancer Patients and the Effect of Therapy, Cancer Research, vol. 37, pp. 646-650, 1977.

Li et al., The *Haemophilus ducreyi* cytolethal distending toxin activates sensors of DNA damage and repair complexes in proliferating and non-proliferating cells, Cellular Microbiology, vol. 4, pp. 87-99, 2002.

Liggett et al., Methylation patterns of cell-free plasma DNA in relapsing-remitting multiple sclerosis, Journal of Neurological Sciences, vol. 290, pp. 16-21, 2010.

Malickova, Karin et al., Decreased Activity of DNase-I Predisposes to Immune-Mediated Complications in IBD Patients During Anti-TNFA Treatment, Gastroenterology, Abstract 202, vol. 138 (5 Supplement 1), S-37, 2010.

Merkus et al., DNase treatment for atelectasis in infants with severe respiratory syncytial virus bronchiolitis, Eur Respir J, vol. 18, pp. 734-737, 2001.

Moreira VG et al., Usefulness of cell-free plasma DNA, procalcitonin and C-reactive protein as markers of infection in febrile patients, Annals of Clinical Biochemistry, vol. 47, pp. 253-258, 2010.

(56) References Cited

OTHER PUBLICATIONS

Mosca et al., Cell-free DNA in the plasma of patients with systemic sclerosis, Clinical Rheumatology, vol. 28, pp. 1437-1440, 2009.
Mutirangura A., Serum/plasma viral DNA: mechanisms and diagnostic applications to nasopharyngeal an cervical carcinoma, Ann NY Acad Sci., vol. 945, pp. 59-67, 2001.
Nestle & Roberts, An extracellular nuclease from *Serratia marcescens*, J. Biol. Chem., vol. 244, pp. 5213-5218, 1969.
Ngan et al., Remarkable Application of Serum EBV EBER-1 in Monitoring Response of Nasopharyngeal Cancer Patients to Salvage Chemotherapy, Ann. NY Acad. Sci., vol. 945, pp. 73-79, 2001.
Pressler T., Review of recombinant human deoxyribonuclease (rhDNase) in the management of patients with cystic fibrosis, Biologics: Targets & Therapy, vol. 2, pp. 611-617, 2008.
Pulmozyme® (dornase alfa) Inhalation Solution product leaflet, Genetech, Inc., 2005.
Rao KS and Shrivastaw KP, Studies on the synthesis and degradation of DNA in developing and old chick cerebellum, Journal of Neurochemistry, vol. 27, pp. 1205-1210, 1976.
Raz E. et al., Anti-DNA antibodies bind directly to renal antigens and induce kidney dysfunction in the isolated perfused rat kidney, J Immunol, vol. 142, pp. 3076-3082, 1989.
Schapira, Anthony H. V., Mitochondrial disease, Lancet, vol. 368, pp. 70-82, 2006.
Sergeeva L. M., Kliniko-laboratonaya otsenka mukoliticheskogo effekta pulmozima u bolnykh mukovistsidozom, Ekaterinburg, 1999, PhD dissertation in medicine, p. 9, paragraphs 2-3; p. 12, paragraph 4; p. 13, paragraphs 1-2; p. 17, paragraph 4; p. 18, paragraph 1; p. 30, paragraphs 3-4; p. 31, paragraph 2 (Reference in Russian and English Translation).
Shak et al., Recombinant human DNAse I reduces the viscosity of cystic fibrosis sputum, Proc. Natl. Acad. Sci. USA, vol. 87, pp. 9188-9192, 1990.
Shevchuk, N.A., Vremyarazreshenniy Immunofluorescentniy Analiz na DNK i Issledovanie Soderzhaniya DNK v Syvoroike Cheloveka, Voprosi Medicinskoi Khimii, No. 4, 2001 (Reference in Russian and English Translation).
Shimony et al., Cell free DNA detected by a novel method in acute ST-elevation myocardial infarction patients, Acute Cardiac Care, vol. 12, pp. 109-111, 2010.
Simpson G., et al., Successful treatment of empyema thoracis with human recombinant deoxyribonuclease, Thorax, vol. 58, pp. 365-366, 2003.
Supplementary European Search Report for European Patent Appl. No. EP04748955, mailed May 19, 2009.
Supplementary European Search Report for European Patent Appl. No. EP04775224, mailed Oct. 28, 2009.
Supplementary European Search Report for European Patent Appl. No. EP05745412, dated Jul. 10, 2009.
Supplementary European Search Report for European Patent Appl. No. EP03796243, dated Jan. 12, 2010.
Tetz, GV, et al., Effect of DNase and Antibiotics on Biofilm Characteristics, Antimicrobial Agents and Chemotherapy, vol. 53, pp. 1204-1209, 2009.
Tetz VV and Tetz GV, Effect of Extracellular DNA Destruction by DNase I on Characteristics of Forming Biofilms, DNA and Cell Biology, vol. 29, pp. 399-405, 2010.
Tetz, GV, et al., Effect of nucleolytic, proteolytic, and lipolytic enzymes on transfer of antibiotic resistance genes in mixed bacterial communities, Universal Journal of Medicine and Dentistry, vol. 1, pp. 46-50, 2012.
Translation of International Preliminary Report on Patentability for PCT/RU2003/000304, dated Nov. 1, 2005.
Translation of International Preliminary Report on Patentability for PCT/RU2004/000260, mailed Jan. 14, 2006.
Translation of International Preliminary Report on Patentability for PCT/RU2004/000261, mailed Dec. 2, 2005.
Translation of International Preliminary Report on Patentability for PCT/RU2004/000262, mailed Apr. 12, 2006.
Translation of International Preliminary Report on Patentability for PCT/RU2005/000236, mailed Feb. 13, 2008.
Ulrich & Friend, Toxicogenomics and drug discovery: will new technologies help us produce better drugs?, Nature, vol. 1, pp. 84-88, 2002.
Yasuda, Toshihiro et al., Activity Measurement for Deoxyribonucleases I and II with Picogram Sensitivity Based on DNA·SYBR Green I Fluorescence, Analytical Biochemistry, vol. 255, pp. 274-276, 1998.
Ye et al., Quantification of Circulating Cell-Free DNA in the Serum of Patients with Obstructive Sleep Apnea-Hypopnea Syndrome, Lung, vol. 188, pp. 469-474, 2010.
Zaravinos et al., Levosimendan reduces plasma cell-free DNA levels in patients with ischemic cardiomyopathy, J. Thromb. Thrombolysis, vol. 31, pp. 180-187, 2011.
Zhong et al., Presence of mitochondrial tRNA(leu(UUR) A to G 3243 mutation in DNA extracted from serum and plasma of patients with type 2 diabetes mellitus, J. Clin. Pathol., vol. 53, pp. 466-469, 2000.
Extended European Search Report for European Patent Appl. No. EP12170750 dated Aug. 3, 2012.
Extended European Search Report for European Patent Appl. No. EP12170754 dated Aug. 3, 2012.
Extended European Search Report for European Patent Appl. No. EP12170757 dated Aug. 3, 2012.
Favorov, P.V. Issledovaniye kinetiki prevrashchenii DNK pod deistviem DNK-topoizomeraz i DNK-abzimov, author's abstract of PhD thesis in biological sciences, M., pp. 3-4, 1999 (Reference in Russian and English-language translation).
Funakoshi, A, et al., Clinical Investigation of Serum Deoxyribonuclease: II. Clinical Studies of Serum Deoxyribonuclease Activity in Pancreatic Disease, Gastroenterologia Japonica, vol. 14, pp. 436-440, 1979.
Gluhov BM, Znachenije nukleaz v patogeneze neirovirusnyh zabolevanij, Avtoreferat dissertatsii na soiskanie uchenoi stepeni doktora medicinskikh nauk (author's abstract of MD thesis in medical sciences), Novosibirsk, pp. 15-16, 21-26, 1996 (Reference in Russian and English-language translation of pp. 14-17 and 20-27).
Kalandarishvili F., Nakoplenie spontanno povrezhdennoj DNK v ne-i postgepatjektomirovannoj pecheni u staryh krys, Med. Novosti Gruzii, No. 5, pp. 11-12, 1998 (Reference in Russian and English-language translation).
Mel'Nikov D, et al., Voprosy onkologicheskoi pomoschi na etape reformirovaniya zdravookhraneniya, Ekaterinburg, pp. 159-161, 1996 (Reference in Russian and English-language translation).
Nikolenko G. N., Sozdanie rekombinantnykh antitel 17 protiv virusa kleschevogo entsefalita i izuchenie ikh svoystv, Avtoreferat dissertatsii na soiskanie uchenoi stepeni kandidata biologicheskikh nauk (author's abstract of PhD thesis in biological sciences), Koltsovo, pp. 1-2, 19, 1999 (Reference in Russian and English-language translation).
Osivac et al., Reorganizacija DNK i biologicheskoje starenije, Biohimija, vol. 62, pp. 1491-1502, 1997 (Reference in Russian and English-language translation).
Perel'Man MI, et al., Molekuljarnaja medicina i lechenie tuberkuleza, Problemi tuberkuleza, No. 5, pp. 5-7, 2001 (Reference in Russian and English-language translation).
Yastrebova N.E., Razrabotka i izuchenie diagnosticheskikh vozmozhnostei immunofermentnykh test-sistem na osnove antigennykh preparatov zolotistogo stafilokokka i DNK, Avtoreferat dissertatsii na soiskanie uchenoi stepeni kandidata meditsinskikh nauk (author's abstract of PhD thesis in medical sciences), M., pp. 17-18, 1988 (Reference in Russian and English-language translation).
Macanovic et al., "The treatment of systemic lupus erythematosus (SLE) in *NZB/W* F 1 hybrid mice; studies with recombinant murine DNase and with dexamethasone", Clin Exp Immunol., vol. 106, pp. 243-252, 1996.
Sugihara, S. et al., "Deoxyribonuclease treatment prevents bloodborne liver metastasis of cutaneously transplanted tumour cells in mice", Hr. J. Cancer, vol. 67, pp. 66-70, 1993.
Prince, W. S. et al., "Pharmacodynamics of recombinant human DNase I in serum", Clin Exp Immunol, vol. 113, pp. 289-296, 1998.

(56) References Cited

OTHER PUBLICATIONS

Vonmoos, P.L. and Straub, P.W., "Absorption and hematologic effect of streptokinase-streptodornase (varidase) after intracavital or oral administration", Schweiz Med Wochenschr, vol. 109, pp. 1538-1544, 1979, Abstract.

Lecompte, et al., "Detection of free-circulating tumor-associated DNA in plasma of colorectal cancer patients and its association with prognosis", Int. J. Cancer, vol. 100, pp. 542-548, 2002.

Whitchurch, et al., "Extracellular DNA Required for Bacterial Biofilm Formation", Science, vol. 295, p. 1487, 2002.

Deitsch, et al., "Transformation of malaria parasites by the spontaneous uptake and expression of DNA from human erythrocytes", Nucleic Acids Research, vol. 29, pp. 850-853, 2000.

Zaman, et al., "Direct amplification of *Entamoeba histolytica* DNA from amoebic liver abscess pus using polymerase chain reaction", Parasitol. Res., vol. 86, pp. 724-728, 2000.

Pisetsky, D., "Immune response to DNA in systemic lupus erythematosus", Isr. Med. Assoc. J., vol. 3, pp. 850-853, 2001.

Maurer, HR, "Bromelain: biochemistry, pharmacology and medical use", Cell Mol. Life. Sci., vol. 58, pp. 1234-1245, 2001.

Varidase product information from EPGOnline, accessed on Dec. 12, 2011.

European Patent Appl. No. EP06843990, Supplementary European Search Report dated Nov. 23, 2009 and cf Form 1507.

PCT/RU2006/000642 International Preliminary Report in Patentability dated Jul. 7, 2009 and International Search Report.

Dayan, Pharmacological-Toxicological (Expert Report on Recombinant Human Deoxyribonuclease I (rhDNase; Pulmozyme™), Hum. Exp. Toxicol., 13:S2, 1994.

Department of Health and Human Services Food and Drug Administration, Federal Register, vol. 50, No. 240, Friday, Dec. 13, 1985, Part II, excerpt from p. 51104.

Kaprin et al., Prognoz i lechenie bol'nih poverhnostnim rakom mochevogo puziria visokoi stepeni riska, Visokie Tehnologii v Onkologii, Rostov-na-Donu, vol. 3, pp. 149-150, 2000 (Reference in Russian and English-language translation).

Lee, D. Continued marketing of a useless drug ('Varidase') in Panama, Lancet, vol. 335, p. 667, 1990.

Roche, Pulmozyme®, Dornase alfa solution for inhalation 1.0 mg/ml, Data Sheet, 2008.

Varidase Buccal Tablets product information from Lederle Laboratories Inc., Canad. M. A. J., vol. 84, pp. 867-868, 1961.

Vonmoos PL, Straub PW, Absorption and hematologic effect of strptokinase-streptodornase (varidase) after intracavital or oral adminstration, Oct. 27, 1979, pp. 1538-1544, Schweiz.

Lecomte et al., Detection of Free-Circulating Tumor-Associated DNA in Plasma of Colorector Cancer Patients and its Association with Prognosis, International Journal of Cancer 100(5): 542-548 (Aug. 2002).

Whitchurch et al., Extracellular DNA Required for Bacterial Biofilm Formation, Science 295:1487 (Feb. 2002).

Deitsch et al., Transformation of malaria parasited by the spontaneous uptake and expression of DNA from human erythrocytes, Nucleic Acids Research, pp. 850-853, 2001, vol. 29.

Zaman et al., Direct amplification of *Entamoeba histolytica* DNA from amoebic liver abscess pus using polymerase chain reaction, Parasitol Res, 2000, pp. 724-728.

Pisetsky, David, Immune Response to DNA in Systemic Lupus Erythematosus, IMAJ, Nov. 2001, pp. 850-853, vol. 3.

Maurer, HR, Bromelain: biochemistry, pharmacology and medical use, CMLS Cellular and Molecular Life Sciences, 2001, pp. 1234-1245.

* cited by examiner

METHOD FOR TREATING HUMAN DISEASES ASSOCIATED WITH AN INCREASED DEOXYRIBONUCLEIC ACID CONTENT IN EXTRACELLULAR SPACES OF TISSUES AND A MEDICINAL PREPARATION FOR CARRYING OUT SAID METHOD

TECHNICAL FIELD

The invention relates to medicine and can be used for treating and prophylaxis of a wide range of human diseases associated with increased deoxyribonucleic acid content in extracellular spaces of tissues and organs.

The spectrum of such diseases is wide and includes:
diseases of proliferative nature associated with speeded up reproduction and surplus death of own cells, for example—tumorous and hyperplastic processes; high level of extracellular DNA is associated with bad prognosis for such diseases (Lecomte T., et. al., Detection of free-circulating tumor-associated DNA in plasma of colorectal cancer patients and its association with prognosis. Int J. Cancer 2002 Aug. 10; 100(5): 542-8);

diseases of infectious nature associated with reproduction of infectious agent, such as bacterial, viral, fungous, protozoal infections, dysbacteriosis; in etiology of such diseases extracellular DNA is either an independent pathogenic factor (for example in case when infection is caused by DNA-containing viruses) or it contributes to microorganisms growth being a base of extracellular matrix of their colonies (*Extracellular DNA required for bacterial biofilm formation*, Cynthia B Whitchurch et al. Science. 2002 Feb. 22; 295(5559): 1487), or taking part in microorganisms genetic transformation (Transformation of malaria parasites by the spontaneous uptake and expression of DNA from human erythrocytes. Deitsch K., Driskill C, Wellems T.: Nucleic Acids Res. 2001 Feb. 1; 29(3): 850-3), or it complicates the disease course by making a ground for purulent necrotic masses. (Zaman S., et. al. Direct amplification of *Entamoeba histolytica* DNA from amoebic liver abscess pus using polymerase chain reaction, Parasitol Res. 2000 September; 86(9): 724-8.); (With S. Sherry and L. R. Christensen. Presence and significance of desoxyribose nucleoprotein in the purulent pleural exudates of patients. Proc. Soc. Exp. Biol. Med., 1948, 68: 179-84);

diseases resulting from atrophic, degenerative and inflammatory changes in organs and tissues—for example systemic lupus erythematosus; here the extracellular DNA is one of the key factors of disease pathogenesis (Pisetsky D. S., Immune response to DNA in systemic lupus erythematosus. Isr Med Assoc J., 2001 November; 3(11): 850-3);

DNA originating from dying cells can speed up ageing process and tissues atrophy, U.S. Pat. No. 6,524,578 B1.

BACKGROUND ART

Well-known are treatment methods of a range of listed diseases by enteral introduction of certain enzymes; the patent CA 2394856 A1 particularly describes enteral introduction of enzymes which destroy surface proteins, lipids and carbohydrates for treating infectious diseases. This method doesn't provide destruction of deoxyribonucleic acids as one of the basic components of both intercellular matrix of growing microorganisms and purulent detritus masses. That's why this method isn't effective enough for treating infectious diseases.

Well-known is a method of treating diseases associated with inflammation. The method consists in oral use of proteolytic and lipolytic enzymes Bromelain, GB 984464 A. The formulations used according to the described method also don't contain any enzymes which destroy deoxyribonucleic acids. Because of poor therapeutic effectiveness this method isn't used in clinical pharmacology as an independent method but as an auxiliary one (Bromelain: biochemistry, pharmacology and medical use, Maurer H. R., Cell Mol Life Sci 2001 August 58: pp. 1234-45).

Well-known is a method of systemic enzyme therapy (SET) based on application of proteolytic enzymes compositions introduced in high doses orally or as enemas (Wrba, H. & Pecher, O. Enzymes: A Drug of the Future. Ecomed Verlagsgesellschaft AG & Co., 1993).

Well-known are also methods of treating human diseases associated with inflammation based on enteral introduction of enzyme complex which contains glycolytic, proteolytic and lipolytic enzymes as well as enzymes which destroy deoxyribonucleic acid (deoxyribonucleases, DNASes), GB 1005985 A.

The patent GB1005985 A describes a method of inflammatory diseases treatment consisting in oral introduction of enzymes combination, including streptodornase (streptococcal DNASE) and chemical anti-inflammatory substances; the patent indicates that use of proteolytic enzymes obtained from pancreas is preferable; the conclusion is also done that the dose of used enzymes doesn't influence the treatment efficacy.

Among the above known methods of treatment based on enteral use of DNASE enzymes the closest to the claimed one is a method of treatment of wide range of inflammation-associated diseases based on oral introduction of DNASE enzyme by taking Varidase tablets containing complex of streptokinase and streptodornase (DNASES). The treatment method is based on oral introduction of 4-8 Varidase tablets per day for treatment of some inflammation-associated diseases (ROTE LISTE Buch 2004; ISBN 3-87193-286-8, Rote Liste Service GmbH), and was commonly used: Continued marketing of a useless drug ('Varidase') in Panama. (Lee D., Lancet 1990 March, pp. 335: 667).

The main drawback of this method is low therapeutic and prophylactic efficacy of both treatment of gastrointestinal tract disorders and treatment of other organs diseases. The reason is lack of enzyme absorption into the system circulation. It is particularly mentioned in the article: Orally and rectally administered streptokinase. Investigation of its absorption and activity; (Oliven A., Gidron E.; Pharmacology, 1981 vol. 22: pp. 135-8).

Well-known is a medical preparation for oral administration (Varidase) containing streptococcal enzymes streptokinase (proteolytic enzyme) and streptodornase-streptococcal deoxyribonuclease. The preparation contains 10000 units of streptokinase and 2500 units of streptodornase in one tablet (ROTE LISTE Buch 2004; ISBN 3-87193-286-8. Rote Liste Service GmbH).

This preparation is selected as the prototype of the claimed medical preparation.

Low efficacy of the preparation became one of the main reasons that Varidase tablets were taken out of production, and their marketing authorizations were, cancelled in many countries around the world, particularly, in USA. One of the arguments was their pharmacological inefficiency (Department of Health and Human Services Food and Drug Administration; Federal Register, Vol. 50, N240; Dec. 13, 1985).

SUMMARY OF THE INVENTION

The ground of this invention according to claims 1-7 is provided by creation of effective method for treating human diseases associated with increased deoxyribonucleic acid content in extracellular spaces of tissues and organs.

According to the invention (claims 1-7) this problem is solved in the following way: the method for treating human diseases associated with increased deoxyribonucleic acid content in extracellular spaces of tissues and organs, by enteral administration of DNASE enzyme wherein said enzyme is introduced in doses from 20 000 to 500 000 Kunz units per 1 kg of the body mass per day. According to the method DNASE enzyme can be introduced orally; according to the method dosage form can provide enzyme release in oral cavity; according to the method dosage form can provide enzyme release in stomach; according to the method dosage form can provide enzyme release in small intestine; according to the method dosage form can provide enzyme release in large intestine; according to the method DNASE enzyme can be introduced rectally.

The ground of this invention according to claims 8-13 is provided in the following way: the medical preparation for treating human diseases associated with an increased deoxyribonucleic acid content in extracellular spaces of tissues and organs contains bioactive substance-DNASE enzyme. The content of DNASE enzyme in the single dose of the preparation comprises 25 000-5 000 000 Kunz units; according to claim 8 said preparation can be realized in a form of tablet for oral administration; according to claim 8 said preparation can be realized in a form of capsule for oral administration; according to claim 8 said preparation can be realized in a form of rectal suppository; according to claim 8 said preparation can be realized in a form of chewing gum or oral-buccal pellicle, or sublingual tablet; according to claim 8 said preparation can be dosed as a toothpaste or gel toothpaste, or powder, or oral cavity rinse, chewing gum, oral buccal pellicle or sublingual tablet.

The applicant is not aware of any information sources, which could contain data on identical technical solutions. This fact allows making a conclusion that the said invention corresponds to the criterion "novelty" (N).

The applicant was first to discover that only high doses of the enterally given DNASE enzyme, exceeding 20000 KU/kg/day, can cause reliable increase of DNA-hydrolytic activity in urine, as well as increase of immunoreactive DNASE I enzyme in urine (Table 1). At doses range between 20 000 and 500 000 KU/kg/day such changes have dose-dependent character. Generally it is evidenced that enteral intake of DNASE in high doses results in absorption of catalytically significant quantities of the enzyme into the system circulation. Such discovery makes it possible to create effective oral dosage forms of DNASE for treating human diseases associated with increased deoxyribonucleic acid content in extracellular spaces of tissues and organs, outside the digestive system.

Thanks to invention's distinctive features a new important result is achieved: provided is efficacy and safety of treatment of a wide range of diseases associated with an increased deoxyribonucleic acid content in extracellular spaces of tissues and organs; besides that an important feature of the method is technical simplicity of application (both method and preparation).

The applicant hasn't discovered any information sources containing data about influence of said features on the technical result achieved thanks to them. On the applicants' opinion it testifies that present technical solution corresponds to the criteria "inventive step" (IS).

BRIEF DESCRIPTION OF THE DRAWINGS

Hereinafter the invention is explained by detailed description of its application examples without any references on drawings.

DETAILED DESCRIPTION OF THE PREFERRED EMBODIMENT

The calculated amount of bovine pancreatic DNASE I with activity 3500 KU/mg (made by Seravac; South African Republic) was diluted in water and introduced once per os to 24 healthy volunteers (3 volunteers per one dose). After that total urine was collected during 12 hours; DNA-hydrolytic activity of urine was determined using viscosimetric method; presence of bovine DNASE I in total DNASE I fraction was determined according to electrophoresis picture (gel electrophoresis with isoelectric focusing). Results are given in Table 1.

Application of the invention according to items 8-13 is illustrated by following examples:

Example 1

Solid dosage form of DNASE for oral administration consisting of:

| Dry bovinel pancreatic DNAse | 100 000 Kunz units |
|---|---|
| Magnesium stearate | 2.5 mg |
| Microcrystalline cellulose | 50 mg |
| Lactose | To formation of a 200 mg tablet |

The dosage form is prepared as follows: dry bovine pancreatic DNASE with activity 3500 KU/mg (made by Seravac; South African Republic) (on the basis of 100 000 Kunz units (about 28 mg per 1 tablet)) is mixed with Magnesium stearate, then moistened, granulated. Granulate is mixed with lactose and microcrystalline cellulose in the quantity necessary to obtain 200 mg tablets, and then the mixture is pressed into tablets.

Example 2

Capsular dosage form of DNASE for oral administration consisting of:

| Dry bovine pancreatic DNASE | 1 000 000 Kunz units |
|---|---|
| Magnesium stearate | 2.5 mg |
| Microcrystalline cellulose | 40 mg |

The dosage form is prepared as follows: dry bovine pancreatic DNASE with activity 3500 KU/mg (made by Seravac; South African Republic) (on the basis of 1 000 000 Kunz units (about 280 mg per 1 capsule)) is mixed with Magnesium stearate and Microcrystalline cellulose, then moistened, pressed and granulated. The granulated material is poured into cellulose capsules.

Example 3

Contents of fine dosage form for rectal use (1 suppository of 3 gram).

| | |
|---|---|
| Bovine pancreatic DNASE | 5 000 000 Kunz units |
| Solid fat base | 1600 mg |

Example 4

Dosage form of the preparation in form of plates for oral use (chewing gum).

| | |
|---|---|
| Bovinel pancreatic DNAse | 1 000 000 Kunz units |
| Gum base | 2500 mg |
| Sugar, dextrose, tapioca, wax | to 3000 mg |

Application of the said method is illustrated by following examples:

Example 5

Treatment of Oncological Diseases

The research involved 9 patients taken into the surgery clinic with the diagnosis "breast cancer relapse". All the patients had gone through operative, chemical and radiation treatment of the disease before. By hospitalization all the patients had contraindications to surgery, chemical and radiation treatment. All the patients had measurable liver and/or lungs metastases. All the patients gave their consent on treatment carrying out. At the moment of treatment's start the expected life interval of the patients was not less than 3 months.

Group 1 (3 patients) was treated with placebo capsules during 3 months.

Group 2 (3 patients) was treated with capsules according to the Example 2. The daily dose was 5 000 000 Kunz units during 3 months.

Group 3 (3 patients) was treated with Varidase tablets (made by Wyeth) in maximum recommended dose which is 10 tablets in a day (25000 IU of streptodornase in a day) during 3 months.

One of the patients from Group 3 was hospitalized in 9 weeks after treatment start because she suddenly felt worse, and metastasis was in progress. She died in the hospital on the third day after hospitalization.

In 3 months after treatment start the patients were readmitted to the hospital. All the patients had gone through computed tomography; clinical and biochemical blood study was performed. The general state of health was estimated according to Karnofsky scale.

All the patients from Groups 1 and 3 had enlarged metastatic nodes in liver and lungs; new metastatic centers appeared; Karnofsky index decreased by 30% on average. Three patients of five had noticeable worsening of blood values (decrease of albumin content in serum, intensification of hepatic cytolysis syndrome, anemia and biochemical signs of inflammation).

The repeated tomography of the patients from Group 2 didn't reveal any signs of old metastatic nodes' enlargement; appearance of new nodes was not noted as well.

In one case the Karnofsky index increased on 40%. Two other patients didn't have any changes of the Karnofsky index. All the three patients had increased content of serum albumin and blood hemoglobin.

Example 6

Treatment of Infectious Mononucleosis Caused by EBV DNA-Virus

The research involved 20 patients from 15 to 28 years old with immunologically confirmed diagnosis—"infectious mononucleosis". The patients were divided into 3 groups:

Group 1 (8 patients) was treated with placebo tablets during 5 days and received standard symptomatic therapy (glucocorticoids and antibiotics).

Group 2 (6 patients) was treated with tablets according to the Example 1. The daily dose was 25 000 Kunz units per kg of the body mass during 5 days.

Group 3 (3 patients) was treated with Varidase tablets (made by Wyeth) in maximum recommended dose which is 10 tablets in a day (25000 IU of streptodornase in a day) during 5 days.

Results of treatment see in Table 2.

Example 7

Treatment of Maxilla-Facial Phlegmona

The research involved 15 patients in medium heavy state of health, who were admitted to maxillofacial surgery hospital; the diagnosis was "maxillo-facial phlegmona".

The patients were divided into 3 groups:

Group 1 (5 patients) was treated with placebo tablets during three days and received standard antibacterial therapy during five days (cefotaxim 3 g in a day intramuscularly).

Group 2 (5 patients) was treated with tablets according to the Example 1; the daily dose was 1 500 000 Kunz units (15 tablets) during 3 days. At the same time they received standard antibacterial therapy during 5 days (cefotaxim 3 g in a day intramuscularly).

Group 3 (5 patients) was treated with Varidase tablets (made by Wyeth) in maximum recommended dose which is 10 tablets in a day (25000 IU of streptodornase in a day) during 3 days; at the same time they received standard antibacterial therapy during 5 days (cefotaxim 3 g in a day intramuscularly).

Results of treatment see in table 3.

Example 8

Treatment of Periodontitis

The research involved 30 patients with medium heavy periodontitis. In the beginning of research dental deposit was removed from teeth of each patient; then they were instructed on cleaning according to the standard method—with use of tooth threads and interdental brushes. Patients were divided into 3 groups.

Group 1—10 patients used only Colgate toothpaste later on.

Group 2—10 patients used Colgate toothpaste later on as well as chewing gum with DNAse according to the Example 4 (¼ plate was chewed during 30 minutes 4 times a day) during 4 weeks.

Group 3—10 patients used Colgate toothpaste later on as well as Varidase Buccal Tablets during 4 weeks.

Silness-Loe index (oral hygiene index) and Muellermann index (sulcus bleeding index) were evaluated before the beginning of research and by the end of it.

Results of research see in table 4.

Example 9

Treatment of SLE

The research involved 16 patients with confirmed diagnosis "systemic lupus erythematosus" and symptoms of glomerulonephritis (proteinuria, microhematuria).

All the patients received a standard therapy (nonsteroid anti-inflamatory drugs, chloroquine). Patients from the experimental group (8 persons) were additionally treated with suppositories according to the Example 3; the dose was 250000 Kunz units per kg of the body mass in a day during 15 days. DNA concentration in plasma was studied before the start of treatment and by the end of treatment period. DNA content in plasma of control group patients had not reliably changed. Twice decrease of DNA in plasma was revealed in patients of the experimental group by the end of 15-days treatment course.

Example 10

Treatment of Age-Specific Sperm Motility Impairment

The research involved 18 healthy volunteers—men from 50 to 55 years old. The patients were divided into 3 groups:
Group 1 (7 patients) was treated with placebo-capsules during 30 days;
Group 2 (6 patients) was treated with capsules according to example 2; the daily dose was 35 000 Kunz units per kg of the body mass during 30 days;
Group 3 (5 patients) was treated with Varidase tablets (made by Wyeth) in maximum recommended dose which is 10 tablets in a day (25000 IU of streptodornase in a day) during 5 days.

Sperm motility was studied in sperm samples taken from patients of three groups before the beginning of treatment and by the end of it. Before the beginning of treatment the percentage of mobile spermatozoids in sperm samples of patients from all three groups was 46%-54%. Patients from groups 1 and 3 didn't have any changes in motility of spermatozoids after treatment. Sperm samples of patients from the Group 2 contained 58%-62% of mobile spermatozoids after treatment.

Example 11

Influence of the Treatment According Claimed Method on Frequency of Rifampicin-Resistant Mutants Nasopharynx microflora was sowed in patient treated with Rifampicin (1), as well as in patient treated with Rifampicin simultaneously with treatment according to the said method (2). Seeding was performed on agar medium containing Rifampicin 50 µg/ml. CFU number was estimated by means of serial dilutions with cloning on agar medium without antibiotic.

Results of research see in Table 5.

The table makes clear that the patient treated with antibiotic simultaneously with treatment according to the claimed method had much less bacterial load, and there were only a few Rifampicin-resistant bacterial clones among seeded microflora.

Example 12

Influence of the Said Method on the Number of Gentamycin-Resistant Mutants Sowed Patients Faeces' seeding was performed in patients who had taken gentamycin for treating acute intestinal infection. The seeding was performed the next day after the end of treatment. Hybrid cultures were grown in test-tubes as planctonic growth during 24 hours. The quantity of viable cells was estimated according to CFU (colony forming units) number after 24 hours-growing by subcloning to agar medium with antibiotic (Km, 50 µg/ml), The table 6 shows average results for control patients group (Group A; 3 patients) and group of patients treated simultaneously according to the claimed method (Group B; 3 patients).

The table shows that the patients treated with antibiotic simultaneously with treatment according to the claimed method had much less load of gentamycin-resistant microorganisms.

INDUSTRIAL APPLICABILITY

Well-known materials are used for invention's implementation, what on applicant's opinion determines correspondence of the invention to the criterion "Industrial application" (IA)

Results of Treatment Efficacy Research

TABLE 1

| | Single dose of DNAse (KU/kg) | | | | | | | | |
|---|---|---|---|---|---|---|---|---|---|
| | 0 | 250 | 1000 | 10000 | 20000 | 35000 | 50000 | 100000 | 500000 |
| DNA-hydrolytic activity in urine, KU/ml | 0.11 | 0.13 | 0.09 | 0.085 | 0.9 | 5.2 | 10.3 | 17.0 | 37.9 |
| Presence of bovine pancreatic DNAse I in the total fraction of blood DNAse | − | − | − | − | + | + | ++ | ++ | +++ |

Treatment Results According to Example 6

TABLE 2

| Syndrome | Terms of syndrome disappearance after disease manifestation (days) | | |
|---|---|---|---|
| | group 1 | group 2 | group 3 |
| Fever | 12 | 7 | 11 |
| Peripheral lymphadenopathia | 16 | 9 | 17 |
| Tonsillitis | 15 | 11 | 14 |
| Hepatosplenomegaly | 17 | 12 | 18 |

Treatment Results According to Example 7

TABLE 3

| | Group 1 | Group 2 | Group 3 |
|---|---|---|---|
| Terms of fever disappearance after treatment initiation | day 5 | day 2 | day 5 |
| Terms of wound cleansing after treatment initiation | day 7 | day 3 | day 6 |
| Wound closing after treatment initiation | day 12 | day 7 | day 11 |
| Presence of microorganisms resistant to the antibiotic used | 2 of 5 | 0 | 1 of 5 |

Research Results According to Example 8

TABLE 4

| Groups | Index | Before treatment | After treatment |
|---|---|---|---|
| group 1 | Silness-Loe | 1.77 +\- 0.27 | 1.31 +\- 0.35 |
| | Muellerman | 1.4 +\- 0.55 | 0.65 +\- 0.31 |
| group 2 | Silness-Loe | 1.78 +\- 0.37 | 0.71 +\- 0.38 |
| | Muellerman | 1.35 +\- 0.67 | 0.29 +\- 0.21 |
| group 3 | Silness-Loe | 1.74 +\- 0.35 | 1.23 +\- 0.45 |
| | Muellerman | 1.48 +\- 0.41 | 0.8 +\- 0.32 |

Research Results According to Example 11

TABLE 5

| Patient | CFU number | Number of Rifampicin-resistant clones |
|---|---|---|
| 1 | $(3.7 +/- 0.6) \times 10^9$ | 110 |
| 2 | $(2.0 +/- 0.1) \times 10^8$ | 2-3 |

Research Results According to Example 12

TABLE 6

| | CFU number |
|---|---|
| Group A | $1.8 \times 10^{10}$ |
| Group B | $2.8 \times 10^9$ |

The invention claimed is:

1. A method for treating a disease associated with increased deoxyribonucleic acid content in extracellular spaces of tissues and organs in a human in need thereof, said method comprising enterally administering to said human a DNASE I enzyme, wherein said enzyme is introduced in doses from 20 000 to 500 000 Kunitz units per 1 kg of the body mass per day.

2. The method according to claim 1, wherein the DNASE I enzyme is administered orally.

3. The method according to claim 2, wherein the DNASE I enzyme is contained in a dosage form which provides enzyme release in oral cavity.

4. The method according to claim 2, wherein the DNASE I enzyme is contained in a dosage form which provides enzyme release in stomach.

5. The method according to claim 2, wherein the DNASE I enzyme is contained in a dosage form which provides enzyme release in small intestine.

6. The method according to claim 2, wherein the DNASE I enzyme is contained in a dosage form which provides enzyme release in large intestine.

7. The method according to claim 1, wherein the DNASE I enzyme is administered rectally.

8. A method for treating age-specific sperm motility impairment in a human in need thereof, said method comprising enterally administering to said human a DNASE enzyme, wherein said enzyme is introduced in doses from 20 000 to 500 000 Kunitz units per 1 kg of the body mass per day.

* * * * *